United States Patent
Fu et al.

(10) Patent No.: US 6,576,918 B1
(45) Date of Patent: Jun. 10, 2003

(54) CONTAINER AND METHOD FOR TRANSPORTING A SYRINGE CONTAINING RADIOACTIVE MATERIAL

(75) Inventors: Monty Mong Chen Fu, Canyon Country, CA (US); Bing Bing Zhu, Granada Hills, CA (US)

(73) Assignee: Syncor International Corp., Woodland Hills, CA (US)

( * ) Notice: Subject to any disclaimer, the term of this patent is extended or adjusted under 35 U.S.C. 154(b) by 36 days.

(21) Appl. No.: 09/635,518

(22) Filed: Aug. 9, 2000

(51) Int. Cl.[7] ............................................. G21F 5/018
(52) U.S. Cl. ................. 250/507.1; 250/506.1; 206/364; 206/524.1; 53/449; 53/485; 220/23.87
(58) Field of Search ................. 250/507.1, 506.1; 206/365, 364, 524.1, 524.4; 220/648, 254.1, 23.87; 53/449, 484, 485

(56) References Cited

U.S. PATENT DOCUMENTS

| | | | |
|---|---|---|---|
| 1,576,535 A | * | 3/1926 | Muir ........................ 250/506.1 |
| 2,682,352 A | | 6/1954 | Hawkins |
| 2,812,231 A | | 11/1957 | Zar |
| 3,074,542 A | | 1/1963 | Myerson et al. |
| 3,101,841 A | | 8/1963 | Baldwin |
| 3,149,717 A | | 9/1964 | Castelli |
| 3,272,322 A | | 9/1966 | Ogle |
| 3,294,231 A | | 12/1966 | Vanderbeck |
| D208,080 S | | 7/1967 | Hamilton |
| 3,329,146 A | | 7/1967 | Waldman, Jr. |
| 3,344,787 A | | 10/1967 | Maclean |
| 3,367,488 A | | 2/1968 | Hamilton |
| 3,531,644 A | * | 9/1970 | Koster ....................... 250/507.1 |
| 3,673,411 A | | 6/1972 | Glasser |
| 3,677,247 A | | 7/1972 | Brown |
| 3,882,315 A | | 5/1975 | Soldan |
| 3,971,955 A | | 7/1976 | Heyer et al. |
| 4,081,688 A | | 3/1978 | Fries |
| 4,106,622 A | | 8/1978 | Windischman |
| 4,357,541 A | | 11/1982 | Ernst |
| 4,781,697 A | | 11/1988 | Slaughter |
| 4,846,235 A | | 7/1989 | Handke |
| 4,851,702 A | | 7/1989 | Perlman |
| 4,869,299 A | | 9/1989 | Handke |
| 4,892,525 A | | 1/1990 | Hermann, Jr. |
| 4,917,263 A | | 4/1990 | Korb |
| D324,101 S | | 2/1992 | Reif et al. |
| 5,096,062 A | | 3/1992 | Burkardt et al. |
| 5,099,998 A | | 3/1992 | Curzon et al. |
| 5,145,063 A | | 9/1992 | Lee |
| 5,157,900 A | | 10/1992 | Kupersmit |
| D333,347 S | | 2/1993 | Kemp et al. |
| 5,205,408 A | | 4/1993 | Cobb |
| 5,235,795 A | | 8/1993 | DeBusk |
| 5,245,117 A | | 9/1993 | Withers et al. |
| 5,277,312 A | | 1/1994 | Vumbaca |
| 5,303,836 A | | 4/1994 | Childress |
| 5,323,719 A | | 6/1994 | Withers et al. |
| 5,385,105 A | | 1/1995 | Withers, Jr. et al. |
| 5,417,326 A | | 5/1995 | Winer |
| 5,672,883 A | * | 9/1997 | Reich ........................ 250/507.1 |
| 5,718,689 A | * | 2/1998 | Stevenson ................... 206/365 |
| 5,828,073 A | * | 10/1998 | Zhu et al. ................. 250/506.1 |
| 5,918,443 A | * | 7/1999 | Phillips ....................... 206/365 |

* cited by examiner

*Primary Examiner*—Jack Berman
(74) *Attorney, Agent, or Firm*—Sheppard, Mullin, Richter & Hampton LLP

(57) ABSTRACT

An improved method and apparatus for transporting a syringe containing radioactive material that provides many advantages, including the safe enclosure of the syringe both before and after use, which reduces the possibility of contamination of the radiopharmaceutical pig. The present invention also provides a radiopharmaceutical pig that eliminates the need for a protective plastic outer shell and has a convenient grip. Finally, the present invention allows the user to readily determine if a syringe within a closed sharps container is full or spent without handling the container.

19 Claims, 4 Drawing Sheets

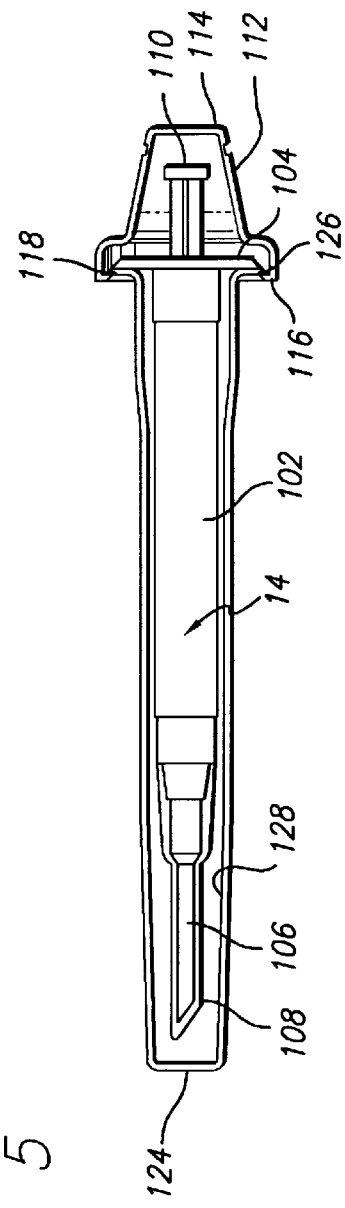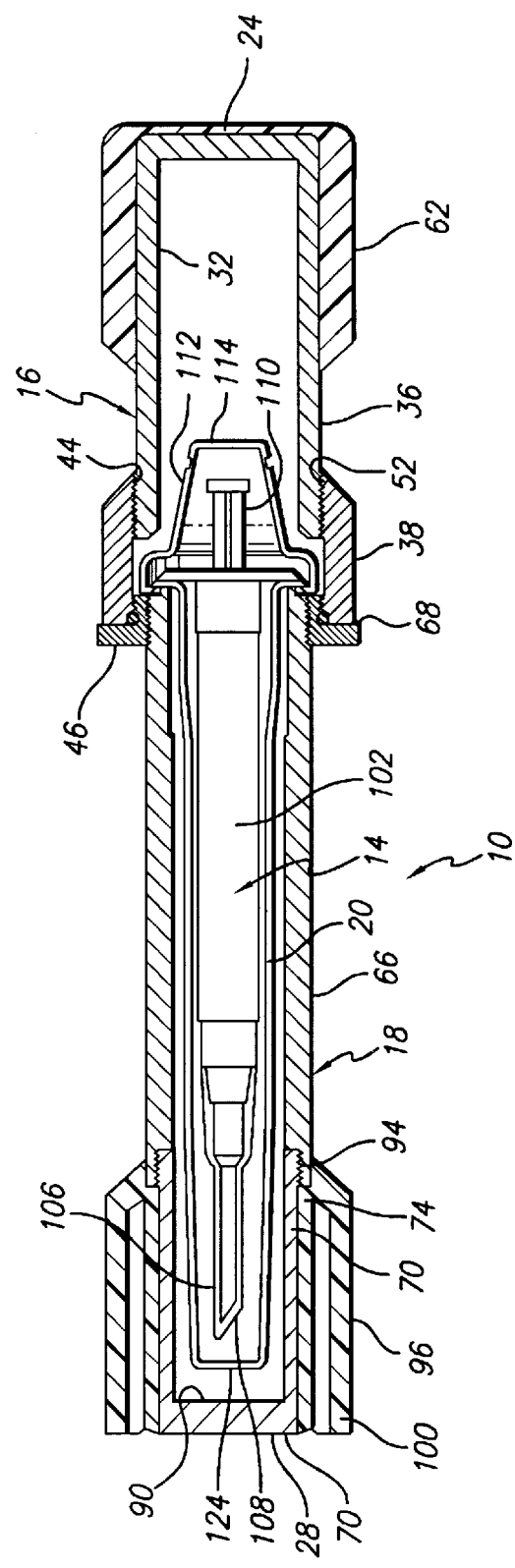

CONTAINER AND METHOD FOR TRANSPORTING A SYRINGE CONTAINING RADIOACTIVE MATERIAL

BACKGROUND OF THE INVENTION

The present invention relates to shielded containers for the transportation of radioactive materials and, more particularly, to shielded containers for the transportation of syringes containing radioactive drugs, or radiopharmaceuticals.

In the nuclear medicine industry, it is well known for pharmacies to deliver syringes containing radioactive drugs to hospitals for injection into a patient. One use for these types of drugs is for the x-ray or other imaging of internal human organs. Pharmacies receive prescription orders and deliver the corresponding radioactive drugs to nearby hospitals for use. Each prescription is individually filled, and each dose of radioactive drug is packaged in a syringe intended for a specific patient.

Radioactive drugs must be carefully handled. Therefore syringes containing such drugs are delivered inside containers offering some degree of radiation shielding. Furthermore, government regulations require syringes to be disposed of in a disposal container that shields others from the risk of injury posed by their sharp, biologically-contaminated hypodermic needles. Such a container, generally referred to herein as a "sharps" container, typically has an inner cavity or chamber that can hold one or more syringes.

One type of conventional delivery container currently used for the delivery of syringes containing radioactive drugs is known as a radiopharmaceutical pig. The radiopharmaceutical pig has a shielded inner chamber suitable for enclosing a syringe that is itself held inside of a sharps container. In particular, the chamber is lined with elemental lead to shield people from the radioactive drug in the syringe. The exterior of the radiopharmaceutical pig is a plastic polystyrene shell. The sharps container has an insert and a cap that can be engaged by two snaps that fit into two aligned slots formed on the insert.

One conventional method for delivering the radioactive syringe uses the devices described above. In particular, at the pharmacy, a sharps container insert is placed in the radiopharmaceutical pig. The syringe is loaded with the required dose of a radioactive drug is placed in the insert, which is nested in the chamber of the radiopharmaceutical pig. The radiopharmaceutical pig is then closed and delivered to the hospital, whereupon the pig is disassembled and the syringe is used according to other, well known, safety standards.

After the dose is injected into the patient, the syringe is referred to as "spent," but generally contains a small amount of residual radioactive drug. In addition to the radioactive contamination, the hypodermic needle of the spent syringe is biologically contaminated from contact with the patient. The spent syringe may then be placed back into the sharps insert and the cap may then be placed on the housing to hold the spent syringe within the sharps container. The radiopharmaceutical pig is reassembled and taken to a disposal area, which may or may not be at the pharmacy.

While the previously discussed radiopharmaceutical pig and sharps container are generally effective, under certain conditions there may be drawbacks associated with such devices. One such drawback is that the snaps on the sharps container cap must be aligned with the slots on the insert in order to attach the cap to the insert. Thus, it may be difficult or more time consuming for a healthcare worker to align the snaps with the slots to attach the cap to the insert.

The conventional cap also is difficult to remove from the insert after it has been attached to the insert. Thus, the cap typically is not installed on the insert at the pharmacy, prior to its delivery to the hospital. Because the insert is not capped, there is a risk that the loaded syringe could leak and that the leaked radioactive drug could escape from the insert if the pig is tilted or inverted. If such contamination occurs, cleaning and disinfecting of the pig will require additional manpower and expense. Such a process is expensive and, therefore, undesirable.

Yet another drawback is related to the difficulty of determining if the syringe in the sharps container is spent or not. If the insert is transparent, the sharps container must be removed from the radiopharmaceutical pig in order for a worker to look through the insert at the syringe. If the insert is not transparent, the sharps container may have to be disassembled to view the syringe. Therefore, a worker may expend excess time in determining whether or not the syringe in the sharps container is spent.

Still another drawback is associated with lead shielding of the radiopharmaceutical pig. The soft nature of lead is not well suited to form threaded engagements, so the pig has two plastic outer shells that threadedly engage each other. The outer shells could crack or break upon impact, thereby rendering the pig unusable. In addition, a cracked pig shell could cause a worker to be exposed to sharp edges formed by the cracked plastic. The lead shielding also is bulky, resulting in a large-sized radiopharmaceutical pig.

Accordingly, there exists a need for an improved radiopharmaceutical pig and/or sharps container that alleviates one or more of the drawbacks identified above.

SUMMARY OF THE INVENTION

The present invention resides in an improved method and apparatus for transporting a syringe containing radioactive material that provides manly advantages, including the safe enclosure of the syringe both before and after use, reduces the possibility of contamination of the radiopharmaceutical pig. The present invention also provides a radiopharmaceutical pig that eliminates the need for a protective plastic outer shell. Finally, the present invention allows the user to readily determine if a syringe within a closed sharps container is full or spent without handling the container.

Particularly, and by way of example only, one embodiment of the invention is a transportation container for a syringe containing a radioactive material. The transportation container includes a body and a grip. The body has an upper end, a lower end, and an interior surface defining an internal chamber sized to enclose the syringe. The internal chamber is surrounded by radiation resistant material. The grip is located on the upper end of the body and has an exterior surface defining an enlarged area to be grasped by the worker.

The container may have a grip that extends around the upper end of the body and the grip may be a separate piece attached by frictional engagement with the upper end of the body. In further details, an enlarged base may be provided on the lower end of the body. The base may have an enlarged bottom end to stabilize the container as it sits on a surface. The transportation container may also include a sharps container sized to enclose the syringe. The internal chamber of the body is sized to enclose the sharps container. The grip may be a separate piece or can be integrally formed into the body. The body of the container may be made of tungsten.

In yet another independent and separate embodiment, a transportation container for a syringe containing a radioactive material is provided. The transportation container includes a body having an upper end, a lower end, and an interior surface defining an internal chamber sized to enclose the syringe. The internal chamber is surrounded by radiation resistant material. Also included is a sharps container having a cap and a housing sized to cooperatively enclose the syringe and fit into the chamber of the body. The cap has a closed end and a mating end and the housing has a closed end and a mating end configured to releasably engage the mating end of the cap without requiring precise alignment of the cap with the housing. In this manner, healthcare workers can easily and conveniently attach and remove the cap without bothering to precisely align any clips or snaps. Further detailed features Stay include providing the cap of the sharps container with a circumferential ridge located around in its mating end and/or providing the housing of the sharps container with a circumferential ridge located around its mating end.

In yet another independent and separate embodiment, a transportation container for a syringe containing a radioactive material is provided. This transportation container is made up of multiple pieces of radiation-resistant material, at least one of which has a reduced diameter so as to reduce costs of manufacture and/or shipping.

Yet another independent and separate embodiment provides a method of transporting a syringe containing a radioactive material to a location for use and confining the syringe within a protective container having a housing that can mate with one of two different-sized caps. The protective container is sized to be enclosed in a radiopharmaceutical pig. The method includes inserting the syringe into the housing of the protective container and attaching one cap to the housing of the protective container to enclose the syringe therein. Next, the radiopharmaceutical pig is assembled to enclose the protective container enclosing the syringe. The radiopharmaceutical pig is transported to the location for use and disassembled whereupon the first cap is removed from the protective container. Next, at least some of the radioactive material is discharged from the syringe, resulting in a spent syringe. The spent syringe is then placed in the housing of the disposal container and the other cap is attached to the housing to enclose the spent syringe therein. Optionally, the disposal container may then be placed within the radiopharmaceutical pig, for transport to a disposal area without exposing the spent syringe.

Finally, yet another independent and separate embodiment provides a method of handling a syringe containing a radioactive material. The method utilizes a protective container having a housing and a cap and includes inserting the syringe into the housing of the protective container and then attaching the cap to the housing of the protective container to enclose the syringe therein, without the need for precisely aligning the cap with the housing. Optionally, the method may also include removing the cap from the housing without damaging either by only moving the cap away from the housing. Because precise alignment of the cap and housing is not needed, it is more convenient for health care workers to use the above method.

Other features and advantages of the present invention will become apparent from the following description of the preferred embodiment, taken in conjunction with the accompanying drawings, which illustrate, by way of example, the principles of the invention.

BRIEF DESCRIPTION OF THE DRAWINGS

The following drawings illustrate the invention. In such drawings.

FIG. 4 is a cross-sectional view of the container of FIG. 1, shown holding a spent syringe and a smaller cap on the inner container;

FIG. 5 is a cross-sectional view of the inner container of the container of FIG. 4.

DESCRIPTION OF THE PREFERRED EMBODIMENT

As shown in the exemplary drawings, the preferred embodiment of the present invention comprises a radiopharmaceutical pig 10 and a sharps container 12 for a syringe 14 holding a radioactive drug. The syringe holding the radioactive drug fits within the sharps container, which, in turn, fits within the radiopharmacetcal pig. The sharps container may be designed to meet U.S. government regulations, such as 29 C.F.R. §1910.1030, for protective containers that house materials having biologically contaminated sharp edges. However, the sharps container design could be modified depending on a particular application.

Figure 1:
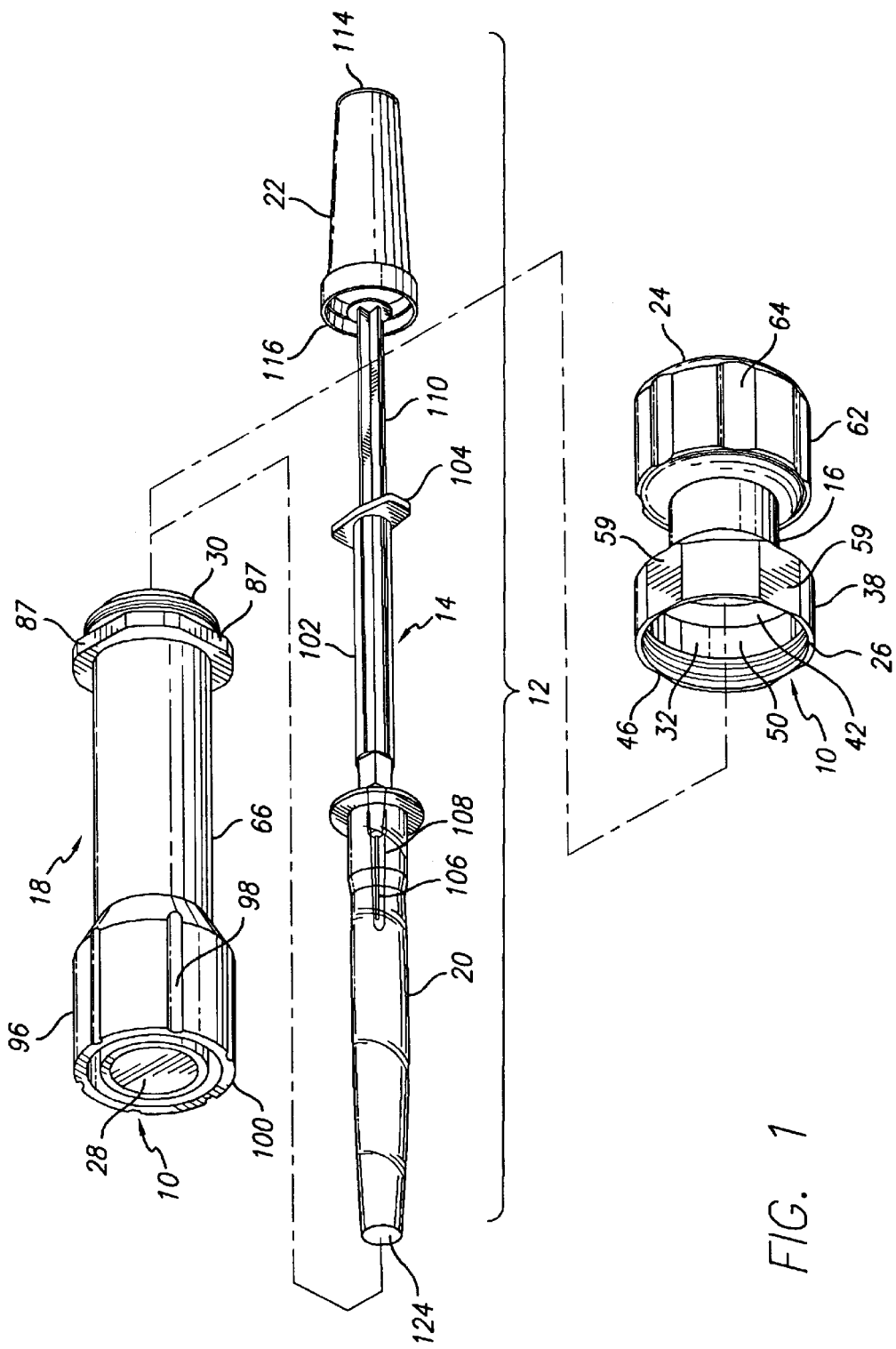
FIG. 1 is an exploded perspective view of the container according to the invention, shown with a syringe containing radioactive material.
Figure 2:
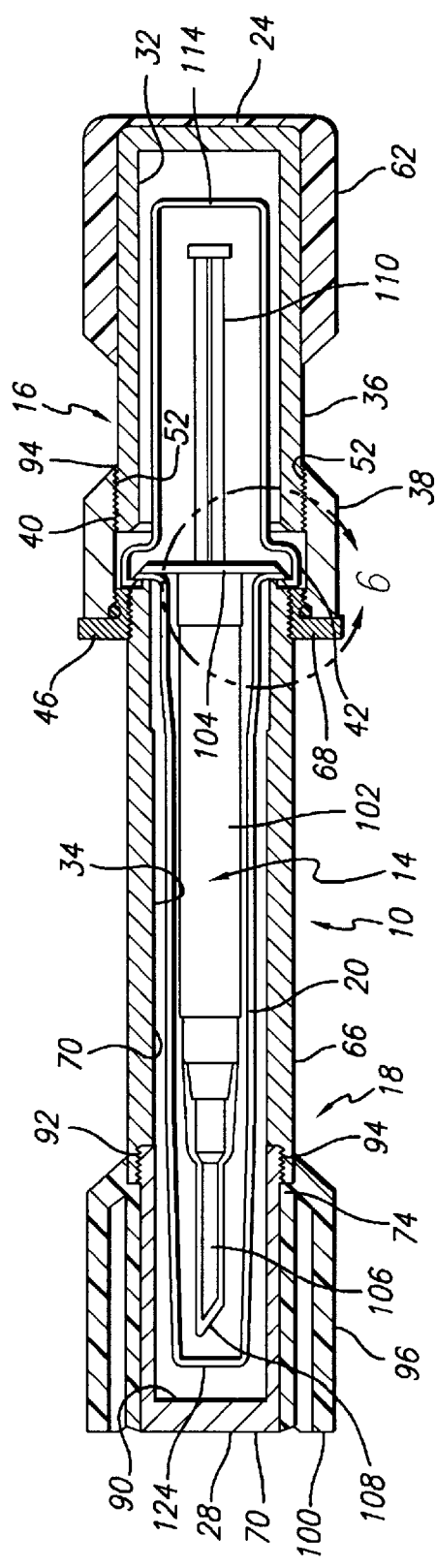
FIG. 2 is a cross-sectional view of the container of FIG. 1.

FIGS. 1, 2, and 4 show the relationship between the components of the radiopharmaceutical pig 10 and the sharps container 12. The radiopharmaceutical pig has a tubular upper shield 16 that screws onto a tubular lower shield 18. the sharps container nests within the upper shield and lower shield. Likewise, the sharps is comprised of a lower insert 20 and an upper cap 22 that cooperatively enclose the syringe 14.

The upper shield 16 of the radiopharmaceutical pig 10 has a generally tubular shape and has a closed end 24 and an open end 26. The lower shield 18 has a generally tubular shape and has a closed end 28 and an open end 30. Both shields have internal cavities 32 and 34 sized to accept at least a portion of the sharps container 12. The upper and lower shields are preferably constructed of tungsten, but any radiation-resistant material may be used, depending on the desired application.

The open end 26 of the upper shield 16 connects to the open end 30 of the lower shield 18 when the radiopharmaceutical pig 10 is assembled. Referring now to FIGS. 1, 2, 4, and 6, the upper shield of the radiopharmaceutical pig has a main body portion 36 and a flanged end portion 38. The main body portion is tubular and has a threaded area 40 on the external surface of its lower end 42. Preferably, the flanged end portion has two open ends 44 and 46 and a passageway 50 therebetween with an inside diameter at least as large as the external diameter of the main body portion. The upper area of the internal passageway of the flanged end portion has threads 52 configured to engage the threads on the main body portion. A waterproof adhesive or sealant can be put on or between these threads to provide for a permanent, secure connection between the main body portion and the flanged end portion. (Other means of attachment could be used, such as welding or other mechanical fasteners, or the flanged end portion may be integrally formed to the main body portion. The lower portion of the passageway of the flanged body portion also has threads 54 configured to engage external threads 56 on the open end 30 of the lower shield, as described below. The flanged end portion may also have wrench flats 59 for use in preventing the rolling of the radiopharmaceutical pig and/or tightening the upper shield to the lower shield. Lastly, the bottom inside edge of the flanged end portion defines a channel 58 to accommodate an O-ring 60 to provide a seal between the upper and lower shields.

Finally, a tubular plastic grip 62 is mounted on the closed end 24 of the upper shield 16. The grip may be mounted by press fit, with adhesive, or mechanical fasteners. The grip has external channels 64 to facilitate gripping of the container by users. The grip also functions as a shield to protect the upper shield from impacts that could crack or damage it. The tubular grip may be made from plastic or rubber, including PVC material.

The lower shield 18 preferably is comprised of three pieces: a tubular body 66, an upper circular flange 68, and a lower end-cap 70. The tubular body has openings on both ends 72 and 74 and a passageway 76 therebetween sized to accept at least a portion of the syringe 14 and/or the sharps container 12 therein. The tubular body has an upper end 72 with a circular wall 78 extending upwardly therefrom to contact an upper ridge 120 on the sharps container insert 20, as will be described below. The upper end of the tubular body also has external threads 82 configured to engage threads 84 on the inside surface of the circular flange. The cross-section of the circular flange is "L" shaped and may have a circular indentation 86 to accept a portion of the O ring 60 therein. The upper portion of the circular flange 8 has external threads 56 configured to engage the threads 54 on the inside of the flanged end portion 38 of the upper shield 16. Wrench flats 87 may be formed on the outside edge of the flange. When assembled, the lower end 26 of the flanged end portion abuts an upper surface 88 located on the horizontal leg of the "L" shaped circular flange. The threads described herein may be connected with adhesive or other mechanical or chemical ways of mounting the components together may be used, as is appropriate for a particular application.

The end cap 70 forming the lower portion of the lower shield 18 is tubular and has a shape similar to the body portion 36 of the upper shield 16. The end cap defines an internal cavity 90 having diameter lesser than that of the lower body 66 of the lower shield. The lower end of the passageway 76 in the body portion has internal threads 92 configured to engage external threads 94 located on the upper portion of the end cap. The cavity in the end cap may be smaller because it may only need to accommodate the narrower portions of the syringe 14. Because less radiation-resistant material is needed to manufacture the end cap, it is believed to be more cost effective to form the lower shield from the body and the end cap, as compared to a one-piece shield having a uniform diameter throughout its entire length.

A tubular plastic base 96 is mounted on the lower end of the lower shield 18. The base may be made of the same material as the plastic grip 62 mounted on the upper shield 16. Channels 98 are formed in the outer surface of the base to facilitate gripping by healthcare workers for the assembly and dis-assembly of the radiopharmaceutical pig 10. The base may be mounted to the lower shield by a press fit, with adhesive, or mechanical fasteners. The base also protects the lower shield from impacts that could cause cracks or other damage. The base has an enlarged lower end 100 sized to stabilize the radiopharmaceutical pig 10 when it is placed on a table top or other work surface.

The syringe 14 has a generally tubular body 102 with a flanged base 104, a hypodermic needle 106, a cap 108, and a plunger 110. The body and needle of the syringe nest within the sharps container housing 20. The plunger fits within the upper shield 16 and the sharps container cap 22. The radiopharmacuetical pig 10 can be configured to hold syringes of various sizes, including those well known in the medical arts.

Figure 3:
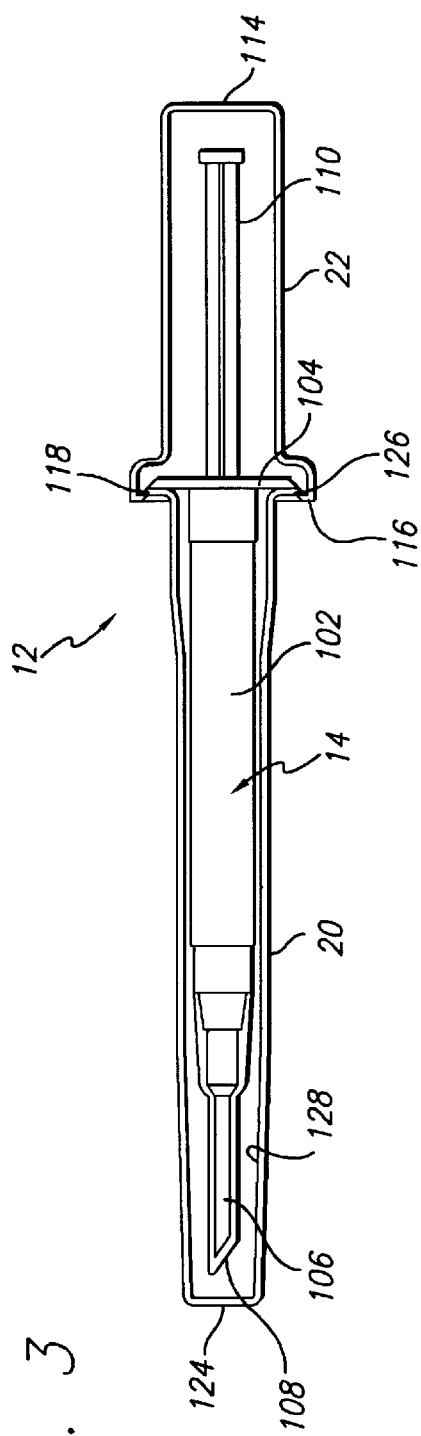
FIG. 3 is a cross-sectional view of the inner container of the container of FIG. 2.

Referring now to FIGS. 1, 3, and 5, the cap 22 of the sharps container 12 preferably has a tubular, cup-like shape to accommodate the plunger 110 of the syringe 14. Likewise, the sharps container housing 20 has a tubular shape to accommodate the body 102 and needle 106 of the syringe. In the alternative or in combination with the cap 22, a similar, but shorter cap 112 may be used. The external dimensions of the caps 22 and 112 and the housing of the sharps container are sized so that they will nest within the upper 16 and lower 18 shields of the radiopharmaceutical pig 10.

Each cap 22 and 112 has a closed end 114 and an open mating end 116 with an inwardly projecting circumferential ridge 118 that will deform as it slides downwardly over an outwardly projecting circumferential ridge 120 on the upper end of the housing 20. Likewise, the ridge 120 on the housing may deform when the ridge 118 of the cap moves downwardly past the ridge on the housing. Each of the ridges has a beveled surface 122 so that the ridges may deform and pass by each other to snap the cap onto the housing. If only the smaller cap 112 is used with the housing for a particular application, cost savings should result because less material is required to make each cap and the lighter-weight caps should cost less to ship.

The caps 22 and 112 of the sharps container 12 may be made from a red-colored polypropylene, PVC, or other plastic material. If the sharps container is intended to comply with certain U.S. government regulations, e.g., 29 C.F R. §1910.1030, it should be labeled appropriately, such as having a red color, to signify that the sharps container contains regulated medical waste. Another way of satisfying this regulation is by labeling the sharps container with the word "biohazard" or the well known international biohazard symbol.

The housing 20 of the sharps container 12 nests within the cavity 34 of the lower shield 18. The housing has a closed end 124, an open mating end 126, and an interior surface that defines an interior cavity 128. The open mating end of the housing has its circumferential ridge 120 that engages the corresponding ridge 118 on either one of the caps 22 and 112. The ridge in the housing also is sized to support the flange 104 of the syringe 14 and rest upon the circular wall 78 extending upwardly from the body 66 of the lower shield 18. The hollow tubular housing is preferably made from a transparent polystyrene or other plastic material. Because the housing material is transparent, the interior of the housing can be viewed without disassembly of the sharps container. The entire housing need not be transparent, rather, the housing may be made from an opaque material having a small, transparent window that provides a view of the interior. The housing also need not be constructed of a transparent material if the contents of the sharps container can be ascertain by other means, such as by the appropriate labeling of the exterior of the sharps container. The housing and the caps may also be constructed from other materials of suitable strength.

The circumferential ridge 118 on the sharps container housing 20 is sized to support the flanged base 104 of the syringe body 102, to support the syringe 14 so that its needle 106 and body are within the cavity 128 of the housing. Because the flanged base of the syringe rests on the ridge of the housing, the syringe is easily inserted with the needle pointing toward the closed end of the housing. Therefore, the fit between the shoulder of the housing and the flanged base of the syringe facilitates placement of the syringe into a position where the needle is immediately shielded within the housing. If the syringe is placed into the housing with its needle pointing upward, the needle poses a threat to persons trying to affix the cap 22 to the housing. Such persons are discouraged from such placement of the syringe because the syringe does not easily rest on the ridge of the housing when it is in such a reversed position. Futhermore, the sharps container 12 cannot be closed with the syringe pointing upward because the caps 22 and 112 preferably are not long enough to accommodate the body 102 and the needle of the syringe. Accordingly, the sharps container is advantageously configured to encourage the placement of the syringe with its needle safely protected within the housing.

Figure 6:
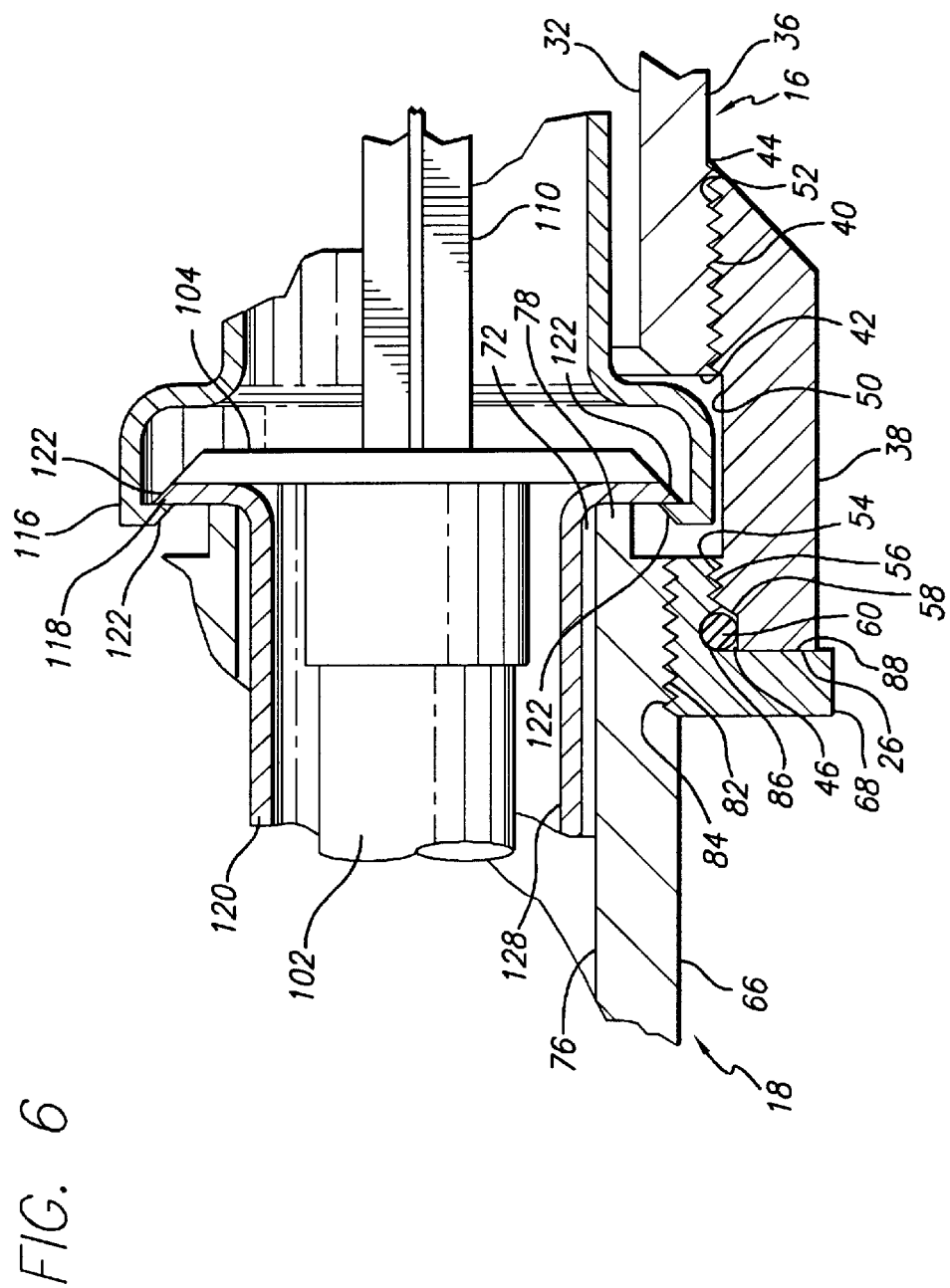
FIG. 6 is a detailed view of the container of FIG. 3, taken about lines 6—6.

The caps 22 and 112 and the housing 20 of the sharps container 12 resist the leakage of the radioactive drug, blood, or other contaminates from within the sharps container. As shown in FIG. 6, the O ring 60 likewise provides a seal between the upper and lower shields 16 and 18 of the radiopharmaceutical pig 10.

Together, the radiopharmaceutical pig 10 and the sharps container 12 can be used to transport and dispose of the syringe 14 without contamination concerns. When a patient needs a dose of a radioactive drug, a healthcare worker, such as a doctor or nurse, transmits a prescription to a pharmacy, where the required drug is packaged in a syringe, using well known medical practices. A label containing information regarding the drug is preferably affixed to the body 102 of the syringe. The following information may be included on the label: the patient's name, the production lot number, the expiration date of the drug, the quantity of the drug, the name of the intended medical procedure, and possibly other relevant information, such as a relevant order number or the drug's radioactive half life. A larger label with similar information also may be affixed to the radiopharmaceutical pig 10. The labels for the syringe and the radiopharmaceutical pig may contain any suitable information, such as words, bar code, or color code. It should be understood that the invention is not limited by the method of encoding and decoding the information contained on the labels, nor by the actual content of the information on the labels.

After the radioactive drug is packaged within the syringe 14 at the pharmacy, the sharps container housing 20 may be placed within the inner cavity 34 of the lower shield 18 of the radiopharmaceutical pig 10. The syringe is then placed into the inner cavity 128 of the sharps container housing so that its capped needle 106 projects toward the closed end 124 of the housing. The larger cap 22 of the sharp container 12 may then be attached to the housing to prevent the syringe contents from contaminating the radiopharmaceutical pig. After the syringe has been used at the hospital, the larger cap 22 may be replaced upon the insert to enclose the spent syringe. Alternatively, the sharps container may not be used to deliver the syringe to the location for use if the pharmacy is content to rely upon the capped needle to prevent contamination of the radiopharmaceutical pig. In another alternative arrangement, the hospital may have a pre-ordered supply of large 22 or small 112 caps for use in enclosing spent syringes. In another embodiment, the short cap could be transported with the radiopharmaceutical pig from the pharmacy.

Next, the upper shield 16 of the radiopharmaceutical pig 10 is positioned above the lower shield 18 of the radiopharmaceutical pig so that the mating ends 26 and 30 of the upper and lower shields are in opposed alignment. The upper and lower shields are then moved together and rotated until the threads 54 of the upper shield engage the threads 56 of the lower shield. As shown in FIG. 2, the now-assembled radiopharmaceutical pig contains the sharps container 12 and the syringe 14 containing the radioactive drug. Once the upper portion 16 and the lower portion 18 of the radiopharmaceutical pig 10 have been joined, the radiopharmaceutical pig is placed in a shipping container (not shown) that may need to meet government regulations for the transportation of radioactive substances.

The shipping container may be transported to the destination of use (most likely a hospital) via motor vehicle, aircraft, hand cart, bicycle, or other delivery method. When the syringe 14 is needed for use, the radiopharmaceutical pig 10 is removed from the shipping container and the upper portion 16 is unscrewed from the lower portion 18, to expose the cap 22 or 112 of the sharps container 12. The cap may be conveniently pulled off of the housing 20 to expose the syringe. The syringe may be easily removed by use of well known safety procedures. The syringe may then be used to inject the patient, thereby discharging the radioactive drug from the syringe. After the injection, the syringe may be biologically contaminated and likely will contain a small amount of residual radioactive drug.

After the injection, the spent syringe 14 is inserted into the inner cavity 128 of the housing 20 of the sharps container 12. The shorter sharps container cap 112 may then be placed over the syringe plunger 110, so that the cap's mating end 116 is in opposed alignment with the mating end 126 of the housing 20. The cap is then moved towards the housing until the circumferential ridges 118 and 120 snap past each other to attach the cap to the housing. Alternatively, the larger cap 22 may be affixed to the housing to enclose the spent syringe.

It should be appreciated that the ridges 118 on the caps 22 and 112 and the housing 20 of the sharps container 12 need not be in a precise alignment in order to connect the cap to the housing. Therefore, a healthcare worker may conveniently put the cap on the housing without bothering to align any clips on a cap with any receptacles on the housing, as is the case with at least one conventional radiopharmaceutical pig and sharps container combination. This feature is intended to save time and allow the worker to focus attention on other more important matters.

After the spent syringe 14 is safely contained within the sharps container 12, the radiopharmaceutical pig 10 is assembled by threadably engaging the upper and lower portions 16 and 18 so that the sharps container is enclosed inside the radiopharmaceutical pig. The assembled radiopharmaceutical pig is placed in a shipping container for transport to the disposal area, which may be at the pharmacy. The shipping container is transported to the disposal area where the radiopharmaceutical pig is disassembled by threadably removing the upper portion from the lower portion. When the upper portion of the radiopharmaceutical pig has been removed, the cap 22 or 112 of the sharps container is exposed because it extends upward from the lower portion of the radiopharmaceutical pig. The sharps container is then removed, which allows the label on the syringe to be read through the transparent housing 20. The information on the label enables a disposal worker to determine the proper disposal container for the syringe within the sealed sharps container. The sharps container, with the spent syringe inside, is disposed of by placing in the particular disposal container for radioactive material having the half-life of the radioactive residual.

A primary advantage of the device described above is that it can be handled easily because of its small size and because of the grip 62 and base 96 on the upper and lower shields 16 and 18. Also, the use of the short cap 112 can automatically inform workers that the sharps container 12 contains a spent syringe 14. Likewise, there is no plastic shell that completely encloses shields 16 and 18. Therefore, breakage concerns relating to such plastic shells are alleviated. Upon opening the radiopharmaceutical pig 10, a person is advantageously protected from the threat of an unshielded needle because the syringe is contained within the sharps container.

Yet another advantage of the present invention is the prevention of the contamination of the radiopharmaceutical pig 10 during the transport of the syringe 14 from the pharmacy to the point of patient treatment. The housing 20 of the sharps container 12 advantageously prevents the inner cavity 34 of the lower shield 18 of the radiopharmaceutical pig from becoming contaminated during this trip. If the syringe leaks, the radioactive drug should collect in the housing, thereby preventing the contamination of the lower shield. An additional level of protection can be had through the use of the cap 22 during the transport of the syringe from the pharmacy to the location of use. Furthermore, once the spent syringe is sealed within the sharps container, the inner cavities 32 and 34 of the upper 16 and lower 18 shield are advantageously protected from contamination while the radiopharmaceutical pig is moved to the disposal area. Accordingly, the invention advantageously saves the expense of the cleaning contaminated radiopharmaceutical pigs.

While a particular form of the invention has been illustrated and described, it will be apparent that various modifications can be made without departing from the spirit and scope of the invention. Thus, although the invention has been described in detail with reference only to the preferred embodiments, those having ordinary skill in the art will appreciate that various modifications can be made without departing from the invention. Likewise, it should be appreciated that the scope of the invention includes methods related to the above disclosure. Accordingly, the invention is not intended to be limited, and is defined with reference to the claims ultimately issued in a patent, and the equivalents thereof.

What is claimed is:

1. A transportation container for a syringe containing a radioactive material, the container to be handled by a worker, the transportation container comprising:
    a body having an upper end, a lower end, and an interior surface defining an internal chamber sized to enclose the syringe, wherein the internal chamber is surrounded by radiation resistant material; and,
    a grip on the upper end of the body spaced apart from a connection point of the upper and lower ends, the grip having an exterior surface defining an enlarged area to be grasped by the worker, wherein the grip is a separate piece formed of an impact resistant material.

2. The transportation container of claim 1, wherein the grip extends around the upper end of the body.

3. The transportation container of claim 2, wherein the grip is attached by frictional engagement with the upper end of the body.

4. The transportation container of claim 1, further comprising an enlarged base disposed about the lower end of the body, wherein the base is enlarged relative to the lower end of the of the body.

5. The transportation container of claim 4, wherein the base has an enlarged bottom end, enlarged relative to an upper portion of the base.

6. The transportation container of claim 5, further comprising a sharps container sized to enclose the syringe, and wherein the internal chamber of the body is sized to enclose the sharps container.

7. The transportation container of claim 6, wherein the body is made of tungsten.

8. A transportation container for a syringe containing it radioactive material, the container to be manually handled by a worker, the transportation container comprising:
    a tubular body formed of tungsten having an upper end, a lower end, and an interior surface defining an internal chamber sized to enclose the syringe, the upper and lower ends each having a threaded opening configured to releasably secure the ends to one another, wherein the internal chamber is surrounded by radiation resistant material; and
    a grip on the upper end of the body, the grip having an exterior surface defining an enlarged area to be grasped by the worker, the grip being a separate piece mounted on the upper end of the body spaced apart from a connection region of the upper and lower ends.

9. The transportation container of claim 8, wherein the grip extends around the upper end of the body.

10. The transportation container of claim 9, wherein the grip is tubular and is attached by frictional engagement with the upper end of the body.

11. The transportation container of claim 8, further comprising a base disposed about the lower end of the body, the base having a diameter greater than the lower end of the body.

12. The transportation container of claim 11, wherein the base is tubular and has an enlarged bottom end, enlarged relative to an upper portion of the base.

13. The transportation container of claim 8, further comprising a sharps container sized to enclose the syringe, and wherein the internal chamber of the body is sized to enclose the sharps container.

14. A method of transporting a syringe containing a radioactive material to a location for use and confining the syringe within a protective container having a housing that can mate with one of two different-sized caps, the protective container itself enclosed in a radiopharmaceutical pig, the method comprising:
    inserting the syringe into the housing of the protective container;
    attaching one cap to the housing of the protective container to enclose the syringe therein;
    assembling the radiopharmaceutical pig to enclose the protective container enclosing the syringe;
    transporting the radiopharmaceutical pig to the location for use;
    disassembling the radiopharmaceutical pig;
    removing the first cap from the protective container;
    discharging at least some of the radioactive material from the syringe, resulting in a spent syringe;
    placing the spent syringe in the housing of the disposal container; and
    attaching the other cap to the housing to enclose the spent syringe therein.

15. The method of claim 14, further comprising:

after the spent syringe is enclosed in the protective container reassembling the radiopharmaceutical pig to contain the protective container holding the spent syringe therein for transport to a disposal area without exposing the spent syringe;

transporting the radiopharmaceutical pig from the location of use to the disposal area;

disassembling the radiopharmaceutical pig;

removing the protective container containing the spent syringe from the radiopharmaceutical pig; and disposing of the protective container containing the spent syringe without exposing the spent syringe.

16. A transportation container for a syringe containing a radioactive material, the transportation container comprising:

a body having an upper end, a lower end, and an interior surface defining an internal chamber sized to enclose the syringe, wherein the internal chamber is surrounded by radiation resistant material; and a sharps container assembly having a housing sized to conformably receive a body portion of the syringe, the housing having a mating end configured to mate with a cap, a first cap configured to mate with the housing to cooperatively enclose the syringe, the first cap sized to accommodate a plunger of the syringe in an extended position, and a second cap configured to mate with the housing to cooperatively enclose the syringe, the second cap sized to accommodate the plunger of the syringe in a spent position; wherein the first cap is mated with the housing when the plunger is in the extended position and the second cap is mated with the plunger in the spent position.

17. The transportation container of claim 16, further comprising a grip formed of a resilient material positioned on the upper end of the body spaced apart from a connection point of the upper and lower ends, the grip having an exterior surface defining an enlarged area to be grasped by the worker.

18. The transportation container of claim 16, further comprising a base disposed about the lower end of the body, the base having a diameter greater than the lower end of the of the body.

19. The transportation container of claim 18, wherein the base has a bottom end enlarged relative to an upper portion of the base.

\* \* \* \* \*

UNITED STATES PATENT AND TRADEMARK OFFICE
CERTIFICATE OF CORRECTION

PATENT NO.    : 6,576,918 B1
DATED         : June 10, 2003
INVENTOR(S)   : Monty Mong Chen Fu et al.

It is certified that error appears in the above-identified patent and that said Letters Patent is hereby corrected as shown below:

Column 2,
Line 38, change "manly" to -- many --
Line 40, change "use, reduces" to -- use, which reduces --

Column 3,
Line 16, change "Stay" to -- may --
Line 18, delete "in"

Column 4,
Line 28, change "radiopharmacetcal" to -- radiopharmaceutical --
Line 38, change "the" to -- The --
Line 39, change "sharps is" to -- sharps container is --
Line 66, change "(Other" to -- Other --

Column 5,
Line 33, change "8" to -- 68 --

Column 6,
Line 64, change "ascertain" to -- ascertained --

Column 7,
Line 16, change "Futhermore" to -- Furthermore --

Column 10,
Line 14, change "it" to -- a --

Signed and Sealed this

Twenty-eighth Day of October, 2003

JAMES E. ROGAN
*Director of the United States Patent and Trademark Office*